(12) United States Patent
Dingler et al.

(10) Patent No.: US 6,255,087 B1
(45) Date of Patent: Jul. 3, 2001

(54) METHOD FOR PRODUCING ALCOHOLS FREE OF ENANTIOMERS

(75) Inventors: Christoph Dingler, Sandhausen (DE); Nicholas John Holman, Nottingham (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/331,404

(22) PCT Filed: Feb. 9, 1998

(86) PCT No.: PCT/EP98/00706

§ 371 Date: Jun. 21, 1999

§ 102(e) Date: Jun. 21, 1999

(87) PCT Pub. No.: WO98/37221

PCT Pub. Date: Aug. 27, 1998

(30) Foreign Application Priority Data

Feb. 21, 1997 (DE) ................................. 197 07 008

(51) Int. Cl.[7] ............................. C12P 17/16; C07C 1/04
(52) U.S. Cl. ............................. 435/118; 435/280
(58) Field of Search ................. 435/118, 119, 435/280

(56) References Cited

FOREIGN PATENT DOCUMENTS

95/10521    4/1995    (WO) .

OTHER PUBLICATIONS

Davis et al., *Appl. and Envir. Mic.*, "Microbial models of mammalian metabolism: Microbial Reduction and Oxidation of Pentoxifylline," Aug. 1984, (48) 327–331.

Imuta et al., *J. Org. Chem.*, "Preparation and absolute stereochemistry of isomeric pyridylethanol and threo–di(2–pyridyl) ethanediol," vol. 43, No. 18, 1978, pp. 3530–3532.

Takeshita et al., *Heterocycles*, "Synthesis of optically active hetero alkylaryl alcohols by baker's yeast," vol. 20, No. 12, 1987, 3051–3054.

*Primary Examiner*—Sandra E. Saucier

(74) *Attorney, Agent, or Firm*—Keil & Weinkauf

(57) ABSTRACT

A process for preparing enantiomerically pure alcohols of the formula I (Ia or Ib)

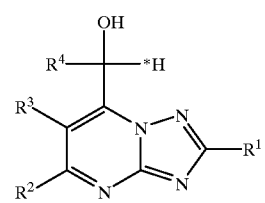

(I)

* = chiral, (Ia or Ib)

where the substituents have the following meanings:

$R^1$
hydrogen or substituted or unsubstituted $C_1$–$C_6$-alkyl, $C_1$–$C_6$-alkoxy or $C_1$–$C_6$-alkanoyl, $R^2$ and $R^3$
independently of one another hydrogen or substituted or unsubstituted $C_1$–$C_6$-alkyl, $C_1$–$C_6$-alkoxy, $C_1$–$C_6$-alkanoyl, $C_1$–$C_6$-alkylthio, $C_1$–$C_6$-alkylsulfinyl or $C_1$–$C_6$-alkylsulfonyl, $R^4$
substituted or unsubstituted $C_1$–$C_6$-alkyl, $C_3$–$C_8$-cycloalkyl, which comprises reducing compounds of the formula II where the substituents $R^1$ to $R^4$ have the abovementioned meanings

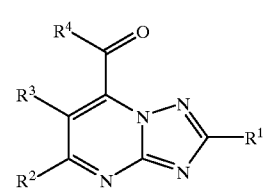

(II)

in aqueous solution in the presence of a carbon source and of a microorganism or of a reducing agent, of a cofactor and of an enzyme, to compounds of the formula I.

6 Claims, No Drawings

METHOD FOR PRODUCING ALCOHOLS FREE OF ENANTIOMERS

This application is a 371 of PCT/EP98/60706 Feb. 9, 1998.

BACKGROUND OF THE INVENTION

1. Field of the Invention

The invention relates to a process for preparing enantiomerically pure alcohols.

Reductions with microorganisms or enzymes are described in a large number of pulications and patents. Only a few studies have been published on the reduction of ketones with heteroaromatic radicals and specifically with heteroaromatic radicals in the position a to the carbonyl group.

Thus, for example, Davis et al. (Appl. Environ. Microbiol. 48 (1984) 327–331) describe the microbial reduction of pentoxifylline (3,7-dihydro-3,7-dimethyl-1-(5-oxohexyl)-1H-purine-2,6-dione), a ketone with a heterocycle in the position γ to the carbonyl group, to the corresponding alcohol (3,7-dihydro-3,7-dimethyl-1-(S-hydroxyhexyl)-1H-purine-2,6-dione). Sources of carbon, nitrogen and phosphorus are necessary for reduction with growing microorganisms. Nothing is said about the enantiomeric purity of the resulting alcohol.

Imuta et al. (J. Org. Chem. 43 (1978) 3530–3532) likewise describe the synthesis in moderate yields and enantiomeric purities of pyridylethanol from the corresponding ketones using growing Cryptococcus macerans cultures. Sources of carbon and nitrogen are also necessary for the reduction in this case.

Takeshita et al. describe in Heterocycles 26 (1987) 3051–3054, the reduction of acetylpyridines with Saccharomyces cerevisiae to pyridylethanol in poor yields.

Optimal microbial reduction of ketones should advantageously comply with a number of conditions such as:

1. high enantiomeric purity
2. high chemical yield
3. high selectivity of the enzyme or microorganism
4. small amounts of catalyst (amounts of enzyme or microorganism)
5. good solubility of precursor and product under the reaction conditions
6. good space-time yield
7. easy purification of the products
8. low-cost synthesis

DETAILED DESCRIPTION OF THE INVENTION

WO 95/10521 claims the chemical synthesis of 1,2,4-triazolo[1,5-a]pyrimidines and the use thereof in pharmaceutical preparations.

It is an object of the present invention to develop a stereoselective synthesis of intermediates of 1,2,4-triazolo[1,5-a]pyrimidines which provides these compounds advantageously with high optical purities and good chemical yields and allows the products to be worked up easily.

We have found that this object is achieved by a process for preparing enantiomerically pure alcohols of the formula I (Ia or Ib)

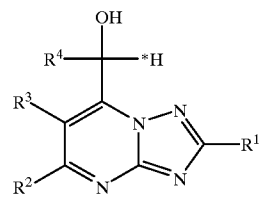

* = chiral, (Ia or Ib)

where the substituents have the following meanings:

$R^1$
  hydrogen or substituted or unsubstituted $C_1$–$C_6$-alkyl, $C_1$–$C_6$-alkoxy or $C_1$–$C_6$-alkanoyl, $R^2$ and $R^3$
  independently of one another hydrogen or substituted or unsubstituted $C_1$–$C_6$-alkyl, $C_1$–$C_6$-alkoxy, $C_1$–$C_6$-alkanoyl, $C_1$–$C_6$-alkylthio, $C_1$–$C_6$-alkylsulfinyl or $C_1$–$C_6$-alkylsulfonyl, $R^4$
  substituted or unsubstituted $C_1$–$C_6$-alkyl, $C_3$–$C_8$-cycloalkyl, which comprises reducing compounds of the formula II where the substituents $R^1$ to $R^4$ have the abovementioned meanings

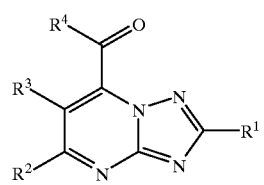

in aqueous solution in the presence of a carbon source and of a microorganism or of a reducing agent, of a cofactor and of an enzyme, to compounds of the formula I.

$R^1$ in formulae I and II is hydrogen or substituted or unsubstituted $C_1$–$C_6$-alkyl, $C_1$–$C_6$-alkoxy or $C_1$–$C_6$-alkanoyl.

The radicals mentioned for $R^1$ have the following meanings, for example:

alkyl branched or unbranched $C_1$–$C_6$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, alkoxy branched or unbranched $C_1$–$C_6$-alkoxy chains such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, alkanoyl branched or unbranched $C_1$–$C_6$-alkanoyl chains such as methanoyl, ethanoyl, propanoyl, 1-methylethanoyl, butanoyl, 1-methylpropanoyl, 2-methylpropanoyl, 1,1-dimethylethanoyl, pentanoyl, 1-methylbutanoyl, 2-methylbutanoyl, 3-methylbutanoyl, 1,1-dimethylpropanoyl, 1,2-dimethylpropanoyl, 2,2-dimethylpropanoyl, 1-ethylpropanoyl, hexanoyl, 1-methylpentanoyl, 1,2-methylpentanoyl, 3-methylpentanoyl, 4-methylpentanoyl, 1,1-dimethylbutanoyl, 1,2-dimethylbutanoyl, 1,3-dimethylbutanoyl, 2,2-dimethylbutanoyl, 2,3-dimethylbutanoyl, 3,3-dimethylbutanoyl, 1-ethylbutanoyl, 2-ethylbutanoyl, 1,1,2-trimethylpropanoyl, 1,2,2-trimethylpropanoyl, 1-ethyl-1-methylpropanoyl and 1-ethyl-2-methylpropanoyl.

Suitable substituents for the alkyl, alkoxy or alkanoyl radicals mentioned for $R^1$ are one or more substituents such as halogen, such as fluorine, chlorine, bromine, cyano, nitro, amino, mercapto, alkyl, alkoxy or aryl.

$R^2$ and $R^3$ in the formulae I and II are, independently of one another, hydrogen or substituted or unsubstituted $C_1$–$C_6$-alkyl, $C_1$–$C_6$-alkoxy, $C_1$–$C_6$-alkanoyl, $C_1$–$C_6$-alkylthio, $C_1$–$C_6$-alkylsulfinyl or $C_1$–$C_6$-alkylsulfonyl.

The radicals mentioned for $R^2$ and $R^3$ have the following meanings, for example:

alkyl branched or unbranched $C_1$–$C_6$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, alkoxy branched or unbranched $C_1$–$C_6$-alkoxy chains such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, alkanoyl branched or unbranched $C_1$–$C_6$-alkanoyl chains such as methanoyl, ethanoyl, propanoyl, 1-methylethanoyl, butanoyl, 1-methylpropanoyl, 2-methylpropanoyl, 1,1-dimethylethanoyl, pentanoyl, 1-methylbutanoyl, 2-methylbutanoyl, 3-methylbutanoyl, 1,1-dimethylpropanoyl, 1,2-dimethylpropanoyl, 2,2-dimethylpropanoyl, 1-ethylpropanoyl, hexanoyl, 1-methylpentanoyl, 1,2-methylpentanoyl, 3-methylpentanoyl, 4-methylpentanoyl, 1,1-dimethylbutanoyl, 1,2-dimethylbutanoyl, 1,3-dimethylbutanoyl, 2,2-dimethylbutanoyl, 2,3-dimethylbutanoyl, 3,3-dimethylbutanoyl, 1-ethylbutanoyl, 2-ethylbutanoyl, 1,1,2-trimethylpropanoyl, 1,2,2-trimethylpropanoyl, 1-ethyl-1-methylpropanoyl and 1-ethyl-2-methylpropanoyl, alkylthio branched or unbranched $C_1$–$C_6$-alkylthio chains such as methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, alkylsulfinyl branched or unbranched $C_1$–$C_6$-alkylsulfinyl chains such as methylsulfinyl, ethylsulfinyl, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl, alkylsulfonyl branched or unbranched $C_1$–$C_6$-alkylsulfonyl chains such as methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

Suitable substituents for the alkyl, alkoxy, alkanoyl, alkylthio, alkylsulfinyl or alkylsulfonyl radicals mentioned for $R^2$ and $R^3$ are one or more substituents such as halogen, such as fluorine, chlorine, bromine, cyano, nitro, amino, mercapto, alkyl, alkoxy or aryl. Fluorine, chlorine, bromine, cyano, nitro, amino, mercapto or alkyl are preferred.

$R^4$ in formulae I and II is substituted or substituted $C_1$–$C_6$-alkyl or $C_3$–$C_8$-cycloalkyl.

The radicals mentioned for $R^4$ have the following meanings, for example:

alkyl branched or unbranched $C_1$–$C_6$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, cycloalkyl branched or unbranched $C_3$–$C_8$-cycloalkyl chains with 3 to 8 carbon atoms in the ring, which may contain other heteroatoms in the ring or in the alkyl chain, such as N, O or S, for example cyclopropyl, cyclobutyl, cyclopentyl, cyclohexyl, cycloheptyl, cyclooctyl, 2-cyclopropylpentane, 5-cyclopropylpentane, 2-cyclobutylbutane, 2,3-dimethyl-3-cyclopropylpropane or 1-methyl-2-cyclopropylbutane.

Suitable substituents for the alkyl or cycloalkyl radicals mentioned for $R^4$ are one or more substituents such as halogen, such as fluorine, chlorine, bromine, cyano, nitro, amino, mercapto, alkyl, alkoxy or aryl. Fluorine, chlorine, bromine, cyano, nitro, amino, mercapto or alkyl are preferred.

Suitable in principle for the process according to the invention (see scheme I) are all microorganisms such as fungi, yeasts or bacteria or enzymes or enzyme systems such as the various alcohol and aldehyde dehydrogenases, the lactate or formate dehydrogenases, preferably alcohol and aldehyde dehydrogenases, able to reduce carbonyl compounds or aldehydes to the alcohols. The microorganisms can be used directly after cultivation (wet biomass) or else after lyophilization (dry matter) for the process according to the invention. The microorganisms or enzymes advantageously used are those able to reduce the compounds of the formula I to the corresponding alcohols with an enantiomeric purity exceeding 85% ee, preferably exceeding 90% ee and very particularly preferably exceeding 95% ee. Examples of suitable microorganisms are organisms of the genera Alcaligenes, Aspergillus, Beauveria, Candida, Cryptococcus, Curvularia, Diplodia, Endomycopsis, Geotrichum, Hansenula, Kloeckera, Kluyveromyces, Lactobacillus, Mucor, Nocardia, Penicillium, Pfaffia, Pichia, Pseudomonas, Rhodococcus, Rhodotorula, Saccharomyces, Schizosaccharomyces, Sporidiobolus, Streptomyces, Torulopsis or Yarrowia. The following species of the abovementioned genera are advantageously used: *Alcaligenes eutrophus, Aspergillus niger, Aspergillus fumigatus, Beauveria bassiana, Candida guilliermondii, Candida lipolytica, Candida membranaefaciens, Candida methylica, Candida parapsilosis, Candida magnoliae, Candida rugosa, Candida utilis, Curvularia falcata, Diplodia gossypina, Cryptococcus macerans, Geotrichum candidum, Hansenula anomala, Hansenula beckii, Hansenula holstii, wingei, Hansenula polymorpha,* Mucor sp., *Nocardia rubropertincta, Pfaffia rhodozyma, Pichia glucozyma, Pichia fermentans, Pichia capsulata, Pichia guilliermondii, Pichia membranaefaciens, Pichia pastoris, Pseudomonas fluorescens, Pseudomonas cepacia, Rhodococcus erythropolis, Rhodococcus ruber, Rhodotorula rubra, Rhodotorula gracilis, Rhodotorula glutinis, Rhodotorula minuta, Rhodotorula termusruber, Saccharomyces cerevisiae, Saccharomyces uvarum, Saccharomyces dairensis, Saccharomyces rouxii, Saccharomyces pastorianus, Saccharomyces kluyveri, Schizosaccharomyces japonicus, Schizosaccharomyces malidevorans, Schizosaccharomyces octosporus, Schizosaccharomyces pombe, Torulopsis enokii, Torulopsis methanothermo* or *Yarrowia lipolytica*. The various yeast genera such as Candida, Hansenula, Kloeckera, Kluyveromyces, Pfaffia, Pichia, Rhodotorula, Saccharomyces, Schizosaccharomyces, Torulopsis or Yarrowia are preferably used. Particularly preferably used are the genera and species *Candida guilliermondii, Candida lipolytica, Candida membranaefaciens, Candida methylica, Candida parapsilosis, Candida magnoliae, Candida rugosa, Candida utilis, Hansenula anomala, Hansenula beckii, Hansenula holstii, wingei, Hansenula polymorpha, Pfaffia rhodozyma, Pichia glucozyma, Pichia fermentans, Pichia capsulata, Pichia guilliermondii, Pichia membranaefaciens, Pichia pastoris, Rhodotorula rubra, Rhodotorula gracilis, Rhodotorula glutinis, Rhodotorula minuta, Rhodotorula termusruber, Saccharomyces cerevisiae, Saccharomyces uvarum, Saccharomyces dairensis, Saccharomyces kluyveri, Saccharomyces rouxii, Saccharomyces pastorianus, Saccharomyces kluyveri, Schizosaccharomyces japonicus, Schizosaccharomyces malidevorans, Schizosaccharomyces octosporus, Schizosaccharomyces pombe, Torulopsis enokii, Torulopsis methanothermo* or *Yarrowia lipolytica*, very particularly preferably the genera and species *Saccharomyces cerevisiae, Saccharomyces uvarum, Schizosaccharomyces japonicus, Pichia fermentans, Hansenula polymorpha, Rhodotorula gracilis, Candida utilis* or *Candida magnoliae*.

For the process according to the invention, the microorganisms are advantageously first cultivated under nitrogen-limited conditions and, after harvesting the cells, for example by centrifugation, used for the process according to the invention. The reduction can be carried out with whole cells, cell digests or crude enzyme extracts obtained from the cells, or purified enzymes. The process is advantageously carried out in aqueous medium in the presence of a carbon source in the case of whole cells or of a reducing agent such as NADH or NADPH and of a cofactor recycling, such as with the aid of formate dehydrogenase and formic acid, and, where appropriate, other enzymes in the case of cell digests, crude extracts or pure enzymes. Addition of further nutrients in the reduction with whole cells, such as a nitrogen source, vitamins or phosphates, is inexpedient because unwanted side reactions are observed under these conditions, for example, which may result in deficient product quality or else workup problems. Suitable as carbon source for the microorganisms are all carbon sources able to provide the cells with the reducing equivalents necessary for the reduction. Examples of carbon sources which may be mentioned here are mono- or disaccharides such as glucose, mannose, maltose, sucrose, primary or secondary alcohols such as methanol, ethanol, propanol, polyols such as glycerol, lower carboxylic acids such as lactic acid, malic acid or amino acids such as glutamate. In the case of glucose, about 10 g of carbon source are required per gram of alcohol (formula I) formed.

Conversion of the precursor with microorganisms in aqueous solution in the presence of a carbon source has the advantage that neither precursor nor product is metabolized and no by-products are formed.

The reaction can be carried out in pure water or in aqueous buffers without addition of other solvents or solvent mixtures. To improve the solubility of the precursor (formula II), it is possible to add water-miscible organic solvents such as THF, acetonitrile, DMF, DMSO, dimethylacetamide, primary or secondary alcohols, carboxylic acids, lactones such as γ-butyrolactone, which are able to improve the solubility of the precursor, to the reaction.

The reaction is advantageously carried out at from 0° C. to 50° C., preferably from 10° C. to 45° C., particularly preferably from 15° C. to 40° C.

The reaction times depend on the substrate, microorganism or enzyme and are from 1 to 72 hours, preferably from 1 to 48 hours. The space-time yield in the reaction is in the range from 5 to 150 g/l/d, preferably from 30 to 100 g/l/d, corresponding to a product formation rate of from 0.5 to 5 g per gram of yeast per day. The yields of isolated product (I) are in the range from 50 to 100%, with a conversion of from 50 to 100%, preferably 80 to 100%. The product concentration at the end of the reaction is in these cases in the range from at least 1 to 40 g/l, preferably from 5 to 30 g/l.

The enantiomer (S alcohol=formula Ia or R alcohol=formula Ib) of the product (formula I) formed depends on the microorganism or enzyme.

The progress of the reaction can easily be followed by conventional methods, for example by gas chromatography after extraction of the product with an organic solvent such as ethyl acetate.

The reaction is preferably carried out under aerobic conditions, ie. with aeration in the case of conversion with microorganisms, preferably with gentle aeration. However, conversion under anaerobic conditions is also possible.

The precursor concentration should advantageously be kept at from 50 to 100% of the maximum solubility of the precursor in the solution, because the reaction takes place very slowly if the precursor concentrations are too low, and the reaction is inhibited at very high concentration. This is in a range from 0.5 to 20 g/l, for example, for the compound of the formula 1 mentioned in scheme I. For rapid reduction, the precursor should be added in portions to the reaction so that the precursor concentration does not exceed 30 g/l. The process can be carried out continuously or batchwise.

EXAMPLES

Reduction of S-(−)-7-(1-oxoethyl)-1,2,4-triazolo[1,5-a]pyrimidine (1) to S-(−)-7-(1-hydroxyethyl)-1,2,4-triazolo[1,5-a]pyrimidine (2) with various microorganisms (see scheme I) is carried out, unless described otherwise, in water under aerobic conditions in the presence of glucose as sole carbon source at room temperature (23° C.). S-(−)-7-(1-Hydroxyethyl)-1,2,4-triazolo[1,5-a]pyrimidine (2) is suitable as precursor for an enantioselective synthesis of the broad spectrum antiepileptic BTS 72664.

Scheme I: Reduction of

S-(−)-7-(1-oxoethyl)-1,2,4-triazolo[1,5-a]pyrimidine (1) to S-(−)-7-(1-hydroxyethyl)-1,2,4-triazolo[1,5-a]pyrimidine (2) with microorganisms (=MO)

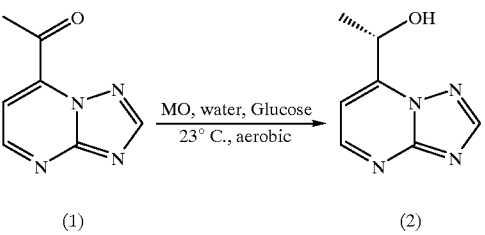

Unless described otherwise, the concentration of precursor and product was determined by gas chromatography. To do this, 250 μl portions of the reaction broth were extracted as sample with 750 μl of ethyl acetate, and the ethyl acetate phase was removed and analyzed by GC (GC column: methylsilicone (HP 1) 12.5 m, injection: 200° C., oven temperature: 50° C. for 3 min, 20° C./min increase to 250° C., 250° C. for 5 min, injector temperature: 250° C., volume injected: 1 μl, detection: FID, integration from 1 min onwards, retention times: precursor 7.95 min, product 8.73 min).

Example 1

Test of Various Yeast Strains

The various yeasts mentioned in Table I were cultured in a medium with a reduced N content (2.5 g/l peptone, 2.5 g/l yeast extract, 20 g/l glucose) until the stationary phase was reached, removed by centrifugation and taken up in the reaction medium (4 g/l precursor (II), 75 g/l glucose, 50 g/l wet yeast biomass, 23° C.). The reaction was incubated with shaking (130 rpm) for 48 h. A further 40 g/l glucose was added after 24 h.

TABLE I

Conversion with various yeast strains

| Organism | Precursor (g/l) | Product (g/l) | Conversion (%) | ee (%) |
|---|---|---|---|---|
| Saccharomtyces cerevisiae (dry yeast) | 0.3 | 2.4 | 89.8 | 98.8 |
| Saccharomyces uvarum CSB 1508 | 0.6 | 1.9 | 75.6 | 98.1 |
| Saccharomyces kluyveri ATCC 22513 | 1.1 | 1.5 | 57.1 | 97.5 |
| Schizosaccharomyces japonicus DSM 70570 | 0.3 | 2.4 | 88.7 | 96.9 |
| Schizosaccharomyces pombe ATCC 38394 | 0.0 | 2.0 | 98.8 | 89.1 |
| Pichia glucozyma ATCC 18938 | 0.1 | 2.2 | 96.6 | 89.6 |
| Pichia fermentans CSB 187 | 0.3 | 2.2 | 88.0 | 99.5 |
| Hansenula polymorpha | 0.4 | 2.1 | 83.9 | 98.2 |
| Rhodotorula gracilis NRRL Y 1091 | 0.0 | 2.9 | 100.0 | 99.7 |
| Candida utilis IFO 0396 | 0.3 | 2.3 | 88.5 | 96.8 |
| Candida magnoliae ATCC 12573 | 0.1 | 2.6 | 97.7 | 98.8 |

Example 2

Reaction Kinetics

Reaction kinetics were determined using dry yeast from the Deutsche Hefewerke in aqueous medium (2 g/l precursor, 100 g/l glucose, 50 g/l yeast). The incubation conditions were condition A: 130 rpm; 150 ml of medium in 250 ml Erlenmeyer flask with two baffles and condition B: 140 rpm; 50 ml of medium in 250 ml Erlenmeyer flask. Both batches were incubated at 23° C.

TABLE II

Reaction kinetics with dry yeast

| | Condition A | | Condition B | |
|---|---|---|---|---|
| Time (h) | Precursor (g/l) | Product (g/l) | Precursor (g/l) | Product (g/l) |
| 0h | 2.0 | 0.0 | 2.0 | 0.0 |
| 1h | 1.8 | 0.2 | 1.9 | 0.2 |
| 2h | 1.7 | 0.3 | 1.8 | 0.3 |
| 3h | 1.6 | 0.5 | 1.5 | 0.6 |
| 4h | 1.4 | 0.7 | 1.4 | 0.7 |
| 5h | 1.2 | 0.9 | 1.2 | 0.8 |
| 6h | 1.0 | 1.0 | 1.0 | 1.0 |
| 7h | 0.9 | 1.1 | 0.9 | 1.1 |
| 8h | 0.7 | 1.2 | 0.8 | 1.3 |
| 23h | 0.1 | 1.9 | 0.1 | 1.9 |

Example 3
Effect of the Precursor Concentration 50 g/l dry yeast (Deutsche Hefewerke) were incubated with 100 g/l glucose in a standard batch (see above) at 130 rpm. After 15 h, a further 100 g/l glucosa (see Table III, 2, 4 and 8 g/l precursor) or 50 g/l glucosa (see Table III, 10 g/l glucose) were added.

TABLE III

Effect of the precursor concentration (Deutsche Hefewerke)

| Precursor initially present (g/l) | Time (h) | Precursor (g/l) | Product (g/l) |
|---|---|---|---|
| 2 | 14 | 0.39 | 1.76 |
| | 23 | 0.31 | 1.77 |
| | 38 | 0.11 | 2.03 |
| 4 | 14 | 1.01 | 3.18 |
| | 23 | 0.72 | 3.40 |
| | 38 | 0.24 | 4.01 |
| 8 | 14 | 2.30 | 5.52 |
| | 23 | 1.50 | 6.43 |
| | 38 | 4.48 | 7.77 |
| 10 | 14 | 4.88 | 4.47 |
| | 23 | 2.47 | 6.82 |
| | 38 | 0.59 | 8.94 |

Example 4
Effect of the Precursor Concentration

A standard batch with 50 g/l yeast (Fermipan, dry yeast from Gist-Brocades) and 50 g/l glucose was tested with various precursor concentrations (see scheme I, compound 1) at 130 rpm (see Table IV). Afther 24 h, a further 40 g/l glucose were added to the reaction mixture. Above 20–30 g/l precursor, the yeast activity descreases markedly.

TABLE IV

Effect of the precursor concentration (50 g/l Fermipan)

| Ketone initially present (g/l) | Time (h) | Precursor (g/l) | Product (g/l) |
|---|---|---|---|
| 5 | 14.5 | 0.5 | 4.5 |
| 10 | 14.5 | 1.9 | 8.0 |
| 20 | 14.5 | 6.7 | 10.2 |

Example 5
Effect of the Precursor Concentration

A batch with 25 g/l yeast (Fermipan, dry yeast from Gist-Brocades) and 60 g/l glucose was tested with various precursor concentration (see scheme I, compound 1) at 130 rpm and 31° C. (see Table V). The reaction was carried out in 250 ml Erlenmeyer flasks with 50 ml of medium.

TABLE V

Effect of the precursor concentration (25 g/l Fermipan)

| Ketone initially present (g/l) | Time (h) | Precursor (g/l) | Product (g/l) |
|---|---|---|---|
| 10 | 15 | 1.2 | 8.3 |
| 20 | 15 | 5.0 | 12.8 |
| 10 | 24 | 0.6 | 8.9 |
| 20 | 24 | 3.1 | 14.1 |
| 10 | 39 | 0.3 | 9.3 |
| 20 | 39 | 2.3 | 15.2 |
| 10(*) | 87 | 0.5 | 15.8 |

(*)a further 5 g/l ketone added after 63 h

Example 6
Effect of the Product Concentration

The reaction was carried out with various initial product concentrations in the presence of 25 g/l Fermipan dry yeast, 10 g/l precursor and 60 g/l glucose at 130 rpm and 31° C. (250 ml Erlenmeyer flask with 50 ml of medium) After 15 h, a further 50 g/l glucose was added. Samples were taken after the times indicated in Table VI. The initial amounts of product had no effect on the conversion in the reaction.

TABLE VI

Effect of the product concentration

| Condition: Product initially present (g/l) | Running time (h) | Precursor (g/l) | Product (g/l) | Conversion (%) | Glucose (g/l) |
|---|---|---|---|---|---|
| 10 | 15 | 0.77 | 20.83 | 92.26 | 0.6 |
| 20 | 15 | 0.88 | 30.86 | 91.21 | 3.1 |
| 30 | 15 | 1.16 | 39.58 | 88.40 | 4.,3 |
| 40 | 15 | 1.34 | 49.15 | 86.62 | 52.2 |
| 10 | 40 | 0.36 | 19.89 | 92.26 | 0.3 |
| 20 | 40 | 0.50 | 29.75 | 91.21 | 0.3 |
| 30 | 40 | 0.64 | 41.02 | 88.40 | 28.2 |
| 40 | 40 | 0.63 | 49.54 | 86.62 | 44.1 |

Example 7
Effect of the Product Concentration

The reaction was carried out with various initial product concentrations without added precursor in the presence of 25 g/l Fermipan dry yeast and 60 g/l glucose at 130 rpm and 31° C. (250 ml Erlenmeyer flasks with 50 ml of medium). After 20 h, a further 50 g/l glucose was added. Samples were taken after 48 h, and GC analysis showed complete recovery of the initial amount of product in them, ie. the product was not metabolized.

Example 8
Effect of Temperature 25 g/l Fermipan dry yeast were incubated in a batch with 10 g/l precursor at 130 rpm and 31° C. (250 ml Erlenmeyer flask with 50 ml of medium) for 14.5 hours. It emerged that the reaction can be carried out in a wide temperature range, with a slight maximum at about 32° C.

TABLE VII

Effect of temperature

| Temperature (° C.) | Precursor g/l | Product g/l | Conversion (%) |
|---|---|---|---|
| 24 | 2.1 | 9.1 | 76.3 |
| 28.5 | 1.1 | 9.6 | 86.8 |
| 30 | 1.0 | 9.3 | 87.1 |
| 32 | 0.6 | 9.0 | 91.1 |
| 37 | 0.6 | 8.5 | 90.9 |

Example 9

Effect of the Yeast Concentration

The effect of the yeast concentration on the reduction was tested. To do this, 50 g/l glucose, 10 g/l precursor (II) in water were introduced into a batch, and various amounts of yeast (Fermipan dry yeast) were employed for the reaction. The batches were incubated with shaking (140 rpm) at 30° C. Samples were taken and analyzed after the times indicated in Table VIII. As the yeast concentration increases, a given amount of precursor can be converted more quickly. No saturation was detectable in the tested range.

TABLE VIII

Effect of the yeast concentration on the reduction

| Yeast concentration (g/l) | Time (h) | Precursor (g/l) | Product (g/l) | Conversion (%) | Glucose (g/l) |
|---|---|---|---|---|---|
| 12.5 | 3 | 8.2 | 1.2 | 13.2 | 41.5 |
| 25 | 3 | 6.8 | 2.5 | 26.8 | 20.3 |
| 50 | 3 | 4.9 | 5.1 | 50.7 | 0 |
| 100 | 3 | 3.6 | 7.2 | 66.9 | 0 |
| 12.5 | 5.5 | 7.5 | 2.1 | 21.7 | 32.0 |
| 25 | 5.5 | 5.3 | 4.6 | 46.3 | 0 |
| 50 | 5.5 | 3.0 | 6.4 | 67.8 | 20.2 |
| 100 | 5.5 | 1.7 | 9.4 | 84.6 | 8.9 |
| 12.5 | 8 | 6.9 | 2.9 | 29.7 | 17.7 |
| 25 | 8 | 3.5 | 5.8 | 62.2 | 36.1 |
| 50 | 8 | 2.0 | 8.3 | 80.7 | 0. |
| 100 | 8 | 0.9 | 10.1 | 91.5 | 0 |
| 12.5 | 13 | 5.0 | 5.6 | 52.8 | |
| 25 | 13 | 1.4 | 8.7 | 86.0 | 0 |
| 50 | 13 | 0.9 | 10.6 | 92.3 | 0 |
| 100 | 13 | 0.5 | 11.7 | 95.6 | 0 |
| 12.5 | 25 | 3.0 | 8.9 | 74.9 | |
| 25 | 25 | 0.9 | 10.7 | 92.6 | 0 |
| 50 | 25 | 0.5 | 11.8 | 95.7 | 0 |
| 100 | 25 | 0.5 | 12.7 | 96.4 | 0 |

Example 10

Ethanol as Carbon Source

Varius ethanol concentrations indicated in Table IX were tested as carbon source for the reduction. To do this, 25 g/l dry yeast (Fermipan), 5 g/l precursor (II) in water were introduced in a batch, and various ethanol concentrations were employed for the reation. The batches were incubated with shaking (130 rpm) at 30° C. Samples were taken and analyzed after the times indicated in Table IX. It emerged that ethanol is likewise suitable as carbon source for the reduction, although the reaction is distinctly slower.

TABLE IX

Ethanol as carbon source

| Ethanol initially present (g/l) | Time (h) | Ethanol (g/l) | Precursor (g/l) | Product (g/l) | Conversion (%) |
|---|---|---|---|---|---|
| 26 | 8 | 25.9 | 4.1 | 1.1 | 21.8 |
| 60 | 8 | 59.2 | 4.4 | 1.2 | 22.0 |
| 142 | 8 | 144.5 | 4.3 | 0.5 | 10.9 |
| 26 | 15 | 18.9 | 3.1 | 2.2 | 41.2 |
| 60 | 15 | 56.3 | 3.8 | 1.7 | 31.3 |
| 142 | 15 | 110.5 | 4.0 | 0.7 | 14.1 |

We claim:

1. A process for preparing enantiomerically pure alcohols of the formula I (Ia or Ib)

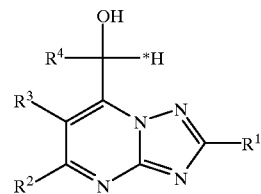

(I)

* = chiral where the substituents have the following meanings:

$R^1$
hydrogen or substituted or unsubstituted $C_1$–$C_6$-alkyl, $C_1$–$C_6$-alkoxy or $C_1$–$C_6$-alkanoyl, $R^2$ and $R^3$
independently of one another hydrogen or substituted or unsubstituted $C_1$–$C_6$-alkyl, $C_1$–$C_6$-alkoxy, $C_1$–$C_6$-alkanoyl, $C_1$–$C_6$-alkylthio, $C_1$–$C_6$-alkylsulfinyl or $C_1$–$C_6$-alkylsulfonyl, $R^4$
substituted or unsubstituted $C_1$–$C_6$-alkyl, $C_3$–$C_8$-cycloalkyl, comprising reducing compounds of the formula II where the substituents $R^1$ to $R^4$ have the abovementioned meanings

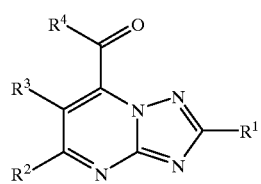

(II)

in aqueous solution in the presence of
a) a carbon source and of a microorganism selected from the group consisting of yeasts, fungi or bacteria or
b) of a reducing agent or
c) of a cofactor and of an alcohol dehydrogenase enzyme, to compounds of the formula I.

2. The process of claim 1, wherein the process is carried out in the presence of a selectively reducing microorganism selected from the group consisting of yeasts, fungi or bacteria or of a selectively reducing alcohol dehydrogenase enzyme.

3. The process of claim 1, wherein the process is carried out in the presence of a microorganism selected from the group consisting of genera Alcaligenes, Aspergmlus, Beauveria, Candida, Cryptococcus, Curvularia, Diplodia, Endomycopsis, Geotrichum, Hansenula, Kloeckera, Kluyveromyces, Lactobacillus, Mucor, Nocardia, Penicillium, Pfaffia, Pichia, Pseudomonas, Rhodococcus, Rhodotorula, Saccharomyces, Schizosaccharomyces, Sporidiobolus, Streptomyces, Torulopsis, and Yarrowiea.

4. The process of claim 1, wherein the microorganism belongs to the genus Saccharomyces.

5. The process of claim 1, wherein the process is carried out in water as sole solvent or in a water/organic solvent mixture.

6. The process of claim 1, wherein the process is carried out at a temperature in the range from 0° C. to 50° C.

* * * * *

UNITED STATES PATENT AND TRADEMARK OFFICE
CERTIFICATE OF CORRECTION

PATENT NO. : 6,255,087 B1  
DATED : July 3, 2001  
INVENTOR(S) : Dingler et al.

Page 1 of 1

It is certified that error appears in the above-identified patent and that said Letters Patent is hereby corrected as shown below:

<u>Column 13, claim 3,</u>  
Line 3, "Aspergmlus" should be -- Aspergillus --.  
Line 9, "Yarrowiea" should be -- Yarrowia --.

Signed and Sealed this

Eifteenth Day of January, 2002

*Attest:*

*Attesting Officer*

JAMES E. ROGAN  
*Director of the United States Patent and Trademark Office*